United States Patent [19]

Chiknas

[11] 4,360,360
[45] Nov. 23, 1982

[54] CENTRIFUGAL ANALYZER

[75] Inventor: Steven G. Chiknas, Vienna, Va.

[73] Assignee: Baxter Travenol Laboratories, Inc., Deerfield, Ill.

[21] Appl. No.: 250,107

[22] Filed: Apr. 2, 1981

[51] Int. Cl.³ ............................................. G01N 21/07
[52] U.S. Cl. ................................... 23/230 R; 233/26; 422/64; 422/72
[58] Field of Search ................ 422/72, 64, 63, 57, 422/58; 356/246; 233/26, 1 R, 1 E; 23/230 R, 230 B

[56] References Cited

U.S. PATENT DOCUMENTS

| | | | |
|---|---|---|---|
| 3,646,346 | 2/1972 | Catt | 422/57 |
| 3,713,775 | 1/1973 | Schmitz | 422/72 |
| 3,856,470 | 12/1974 | Cullis et al. | 422/72 |
| 3,951,608 | 4/1976 | Trod | 422/64 |
| 4,123,173 | 10/1978 | Bullock et al. | 422/72 |
| 4,226,531 | 10/1980 | Tiffany et al. | 422/72 |
| 4,256,696 | 3/1981 | Soodak | 422/64 |
| 4,263,256 | 4/1981 | Morle | 422/66 |
| 4,297,104 | 10/1981 | Matte | 422/72 |

*Primary Examiner*—Ronald E. Serwin
*Attorney, Agent, or Firm*—Robert A. Benziger; George H. Gerstman; Paul C. Flattery

[57] ABSTRACT

A centrifugal analyzer and method for performing chemical reaction measurements. A cuvette ring (60) is positioned on a rotor (36) encircling a shaft (40). A carrier member (62) defining a central aperture (92) is positioned within the central opening of the cuvette ring (60). The carrier member (62) defines a plurality of slots (100), each of which receives a disposable container-like insert (130). The inserts (130) may carry a precoating of an agent for use in an in vitro diagnostic test. Each insert has a slot (136) for enabling centrifugal transfer of the liquid in the insert through the slot, through the aperture (122) defined by the peripheral wall of the carrier member (62), and into a respective cuvette cell.

34 Claims, 10 Drawing Figures

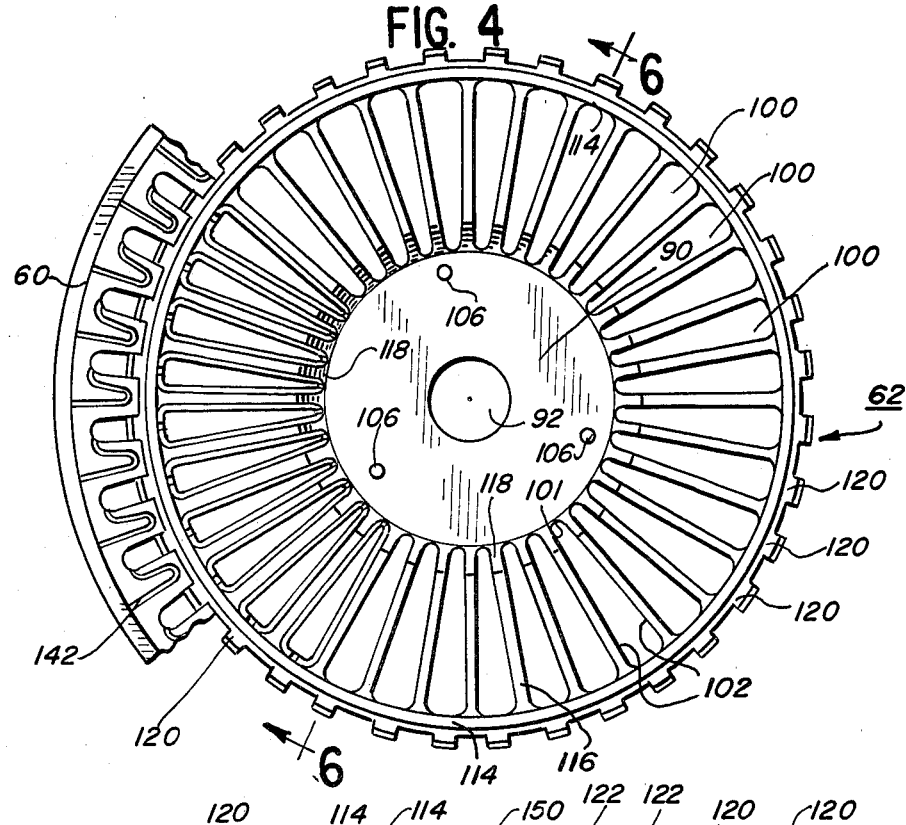
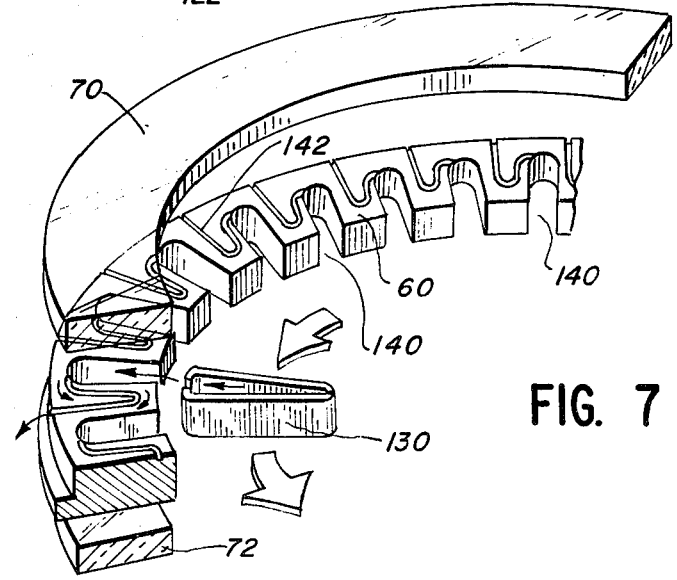

CENTRIFUGAL ANALYZER

TECHNICAL FIELD

The present invention concerns a novel centrifugal analyzer system for performing chemical reaction measurements using centrifugal mixing and sampling techniques.

BACKGROUND ART

In U.S. Pat. No. 3,856,470, a centrifugal analyzer is disclosed in which a transfer disc carrying the constituents to be analyzed is disposed within the central opening of a cuvette ring. The cuvette ring is formed of material having good thermal conductivity and defines cuvette cells into which the constituents are received and may be heated. According to the principles set forth in U.S. Pat. No. 3,856,470, the heating component within the cuvette ring may be regulated and monitored to maintain the temperature of the constituents at a regulated heat level. Further, siphon slots are defined by the cuvette ring in communication with each cuvette cell for exhausting the constituents from the cell after the desired data has been derived. Still further, quartz glass rings may be positioned above and below the cuvette ring to aid in forming the cuvette cells and to provide superior light transmission for the photoresponsive means utilized by the apparatus.

In U.S. Pat. No. 3,856,470, the transfer disc which is interposed within the central opening of the cuvette ring has a number of chambers, with each chamber having two wells which are radially spaced from the axis of rotation of the disc. Separate constituents are disposed in each well, and a passage that is radially spaced from the axis of rotation communicates the separate constituents to a respective cuvette cell.

An apparatus which is being sold commercially having a construction in accordance with the principles of U.S. Pat. No. 3,856,470 is the ROTOCHEM ® IIa centrifugal fast analyzer, manufactured by American Instrument Company, Division of Travenol Laboratories, Inc., Savage, Md.

Known in the art are disposable cuvette systems which lack certain of the advantages of the system disclosed in U.S. Pat. No. 3,856,470. For example, a disposable multi-cuvette rotor for use in a centrifugal analyzer is disclosed in U.S. Pat. No. 4,226,531. The multi-cuvette rotor disclosed therein does not provide for heating, or temperature monitoring, or siphon-exhausting of the reactants from the chambers after the desired data has been derived. In addition, the optical properties are limited by the optical component that is formed as a part of the disposable cuvette rotor.

Another disposable cuvette array for a centrifugal analyzer is disclosed in U.S. Pat. No. 4,123,173. The cuvette array disclosed in this patent is formed entirely of plastic sheet material, and does not provide the temperature regulation that may be provided by the cuvette ring of U.S. Pat. No. 3,856,470. Further, the plastic material forming the cuvette array of U.S. Pat. No. 4,123,173 would generally not have the optical transmissive properties of the quartz glass which may be used with the cuvette ring of U.S. Pat. No. 3,856,470.

It is seen that the heat regulation and excellent optical transmissive benefits of the system of U.S. Pat. No. 3,856,470 are achieved as a result of utilizing a central transfer disc with an outside cuvette ring with which the central transfer disc cooperates. The devices of U.S. Pat. Nos. 4,226,531 and 4,113,173 comprise cuvette arrays formed with a combination of the transfer mechanism and the cuvette. In order to obtain the benefits of disposability, these cuvette arrays have to accept the limitations of the particular plastic cuvette portion for optical transmissiveness and these disposable cuvette arrays cannot be closely heat-monitored as is possible with the separate cuvette ring of U.S. Pat. No. 3,856,470.

It is an object of the present invention to provide a centrifugal analyzer that utilizes a cuvette ring of the type which may be heated, and also employs a disposable carrier member for receiving the constituents to be centrifuged.

Another object of the present invention is to provide a rotatable carrier member adapted to receive a plurality of disposable container-like inserts, with each of the inserts being adapted to receive directly the constituents to be centrifuged, and with the carrier member being adapted for positioning within the central opening of a cuvette ring.

A further object of the present invention is to provide disposable container-like inserts, for positioning within slots defined by a circular carrier member that is indexed and positioned within the central opening of a cuvette ring.

A still further object of the present invention is to provide disposable container-like inserts as aforesaid, in which at least a portion of the insert carries a precoating of an agent for use in an in vitro diagnostic test.

Other objects and advantages of the present invention will become apparent as the description proceeds.

DISCLOSURE OF THE INVENTION

In accordance with the present invention, a centrifugal analyzer is provided which includes a rotor having a rotatable shaft. A circular cuvette ring is provided having an inner wall defining a central opening and slots extending radially outwardly from the central opening. The cuvette ring is adapted for positioning on the rotor encircling the shaft.

A circular carrier member is provided defining a central aperture and is adapted for positioning within the central opening of the cuvette ring, with the shaft extending through the central aperture of the carrier member.

The carrier member defines on its top surface a plurality of slots for receiving constituents to be centrifuged. The carrier member has a peripheral wall for facing the inner wall of the cuvette ring. The peripheral wall defines apertures which communicate with the slots defined by the cuvette ring when the carrier member is positioned within the central opening of the cuvette ring. Each of the apertures is in communication with one of the carrier member slots.

A plurality of disposable container-like inserts are provided. Each of the inserts is adapted for positioning within one of the carrier member slots and is adapted to receive directly constituents to be centrifuged. Each of the inserts has means for enabling centrifugal transfer of the constituents in the insert to an aperture defined by the peripheral wall of the carrier member, for transfer of the constituents into a respective slot defined by the cuvette ring.

In the illustrative embodiment, the carrier member slots comprise generally pie-shaped slots defined by the walls which taper radially outwardly. The carrier member is formed as an integrally-molded plastic member.

In the illustrative embodiment, the inserts carry a precoating of one of the constituents for use in an in vitro diagnostic test. Each insert defines a slot at its entry end for receiving a flushing fluid and also defines a slot at its outer end for enabling the centrifugal transfer of the constituents in the insert to the aperture defined by the peripheral wall of the carrier member.

A more detailed explanation of the invention is provided in the following description and claims, and is illustrated in the accompanying drawings.

BRIEF DESCRIPTION OF DRAWINGS

FIG. 4 is a top plan view thereof, also showing a portion of a cuvette ring in association with the carrier member.

FIG. 5 is an elevational view of the carrier member.

FIG. 7 is a fragmentary, exploded, perspective view of a cuvette ring and an insert, to diagrammatically show the centrifugal fluid flow during use of the apparatus.

DETAILED DESCRIPTION OF THE ILLUSTRATIVE EMBODIMENT

Figure 1:
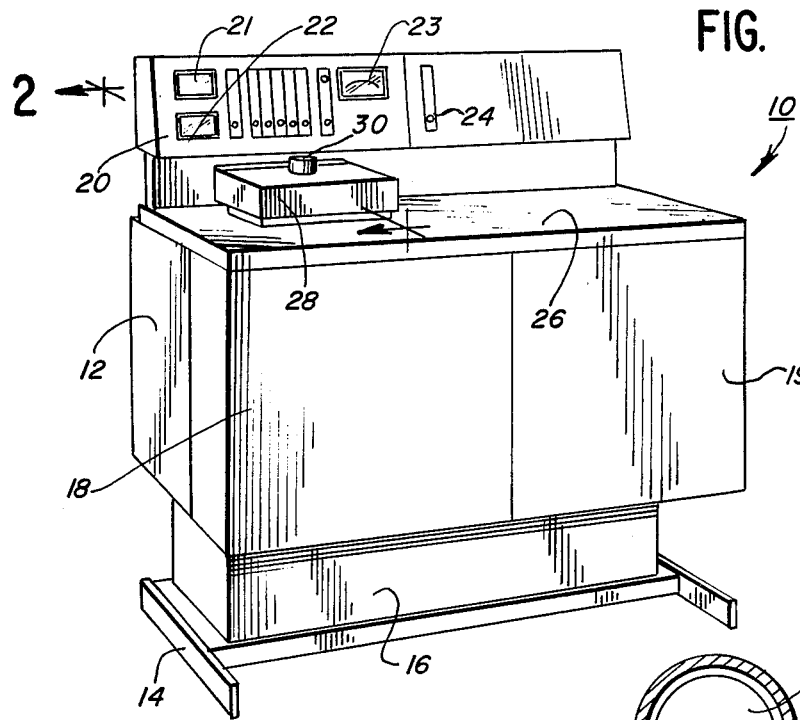
FIG. 1 is a perspective view of a centrifugal fast analyzer constructed in accordance with the principles of the present invention.

Referring to FIG. 1, a centrifugal analyzer 10 is illustrated therein comprising a main console 12 supported on a pedestal 14 and upright member 16, which upright member carries a circuit breaker panel (not shown). On the console 12, a pair of hinged cabinet doors 18 and 19 enclose certain equipment utilized by the fast analyzer, including the drive motor, vacuum trap flasks, a liquid waste container, a wash solution container, filter equipment, etc. A control panel 20 is provided, having a rotor speed meter 21 which indicates the rotor speed, a signal level meter 22 which displays the voltage output of the photodetector for one of the cuvettes, a temperature meter 23 for indicating the temperature of the cuvettes, a power off-on button 24, and various other knobs and buttons for adjusting the signal level output of the photodetector, energizing the rotor motor and controlling its rotational speed, braking the rotor, applying water to the carrier member and cuvettes, applying compressed air to the carrier member, applying a vacuum to the cuvette solutions, setting the temperature controller, adjusting the temperature meter to its set point and calibrating the temperature meter.

A horizontal top surface 26 is provided, with a top cover 28 hinged to top surface 26 for covering the rotor assembly and allowing flushing fluid feed to the rotor assembly via tube 30.

Figure 2:
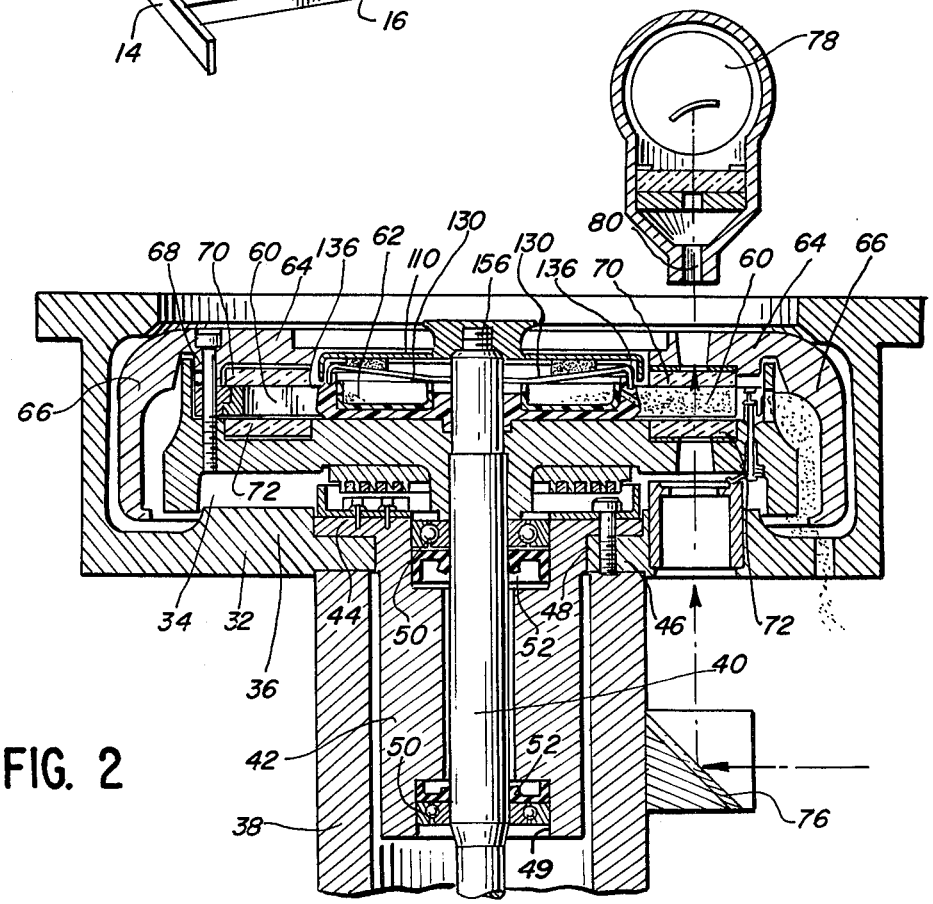
FIG. 2 is an elevational view, primarily in cross-section, of the rotor assembly and associated equipment used in connection with the centrifugal fast analyzer of FIG. 1.

The rotor assembly is illustrated in FIG. 2.

Referring to FIG. 2, it can be seen that a housing having an upper portion 32 provides a chamber 34. A rotor 36 is disposed for movement within the chamber. A lower housing portion 38 serves to enclose a shaft 40 which is received in the upper housing. The shaft at one end is connected to rotor 36 and at the other end is coupled by suitable gear means to a drive motor (not shown).

A collar 42 is supported by the housing members. The collar 42 includes a radial flange 44 which is supported by shoulder 46 of the upper housing. A plurality of set screws 48, only one being shown, circumferentially spaced about the flange 44, are employed to mount the collar 42 and also connect the upper and lower housings.

Collar 42 provides an annular cutout 49 at both the top and bottom. Bearing members 50 secured to the shaft 40 are disposed in each cutout. Sealing members 52 are also disposed in each cutout, and serve to prevent the constituents to be analyzed from passing into the region of the drive motor housing.

Rotor 36 carries a circular cuvette ring 60 and a circular carrier member 62. The rotor assembly includes a top plate 64 which is of annular construction and includes an annular extending skirt portion 66. A plurality of mounting screws 68 circumferentially spaced about the rotor periphery connect together certain of the rotor assembly components including the cuvette ring 60, top plate 64 and rotor 36, to permit rotary movement of the circular cuvette ring 60 within the upper housing. A top glass ring 70 is sandwiched between rotor 36 and cuvette ring 60. Suitable recesses in top plate 64 and rotor 36 are provided for glass rings 70 and 72, respectively. Glass rings 70 and 72 form viewing windows and are preferably formed of quartz, which will permit ultraviolet measurement. Light from a source (not shown) is reflected by mirror 76 toward a photomultiplier tube 78. The photomultiplier tube is supported within a housing that is enclosed to prevent stray light from impinging on the photomultiplier tube, except for light that is reflected via mirror 76, through glass 72, the cuvette cell, glass 70 and light slot 80.

The cuvette ring may be the ring utilized in the ROTOCHEM ® IIa centrifugal fast analyzer manufactured by American Instrument Company, Division of Travenol Laboratories, Inc. A description of a cuvette ring of the type utilizable in connection with the present invention and also a description of a rotor assembly that may be utilized in connection with the present invention is found in U.S. Pat. No. 3,856,470.

Figure 3:
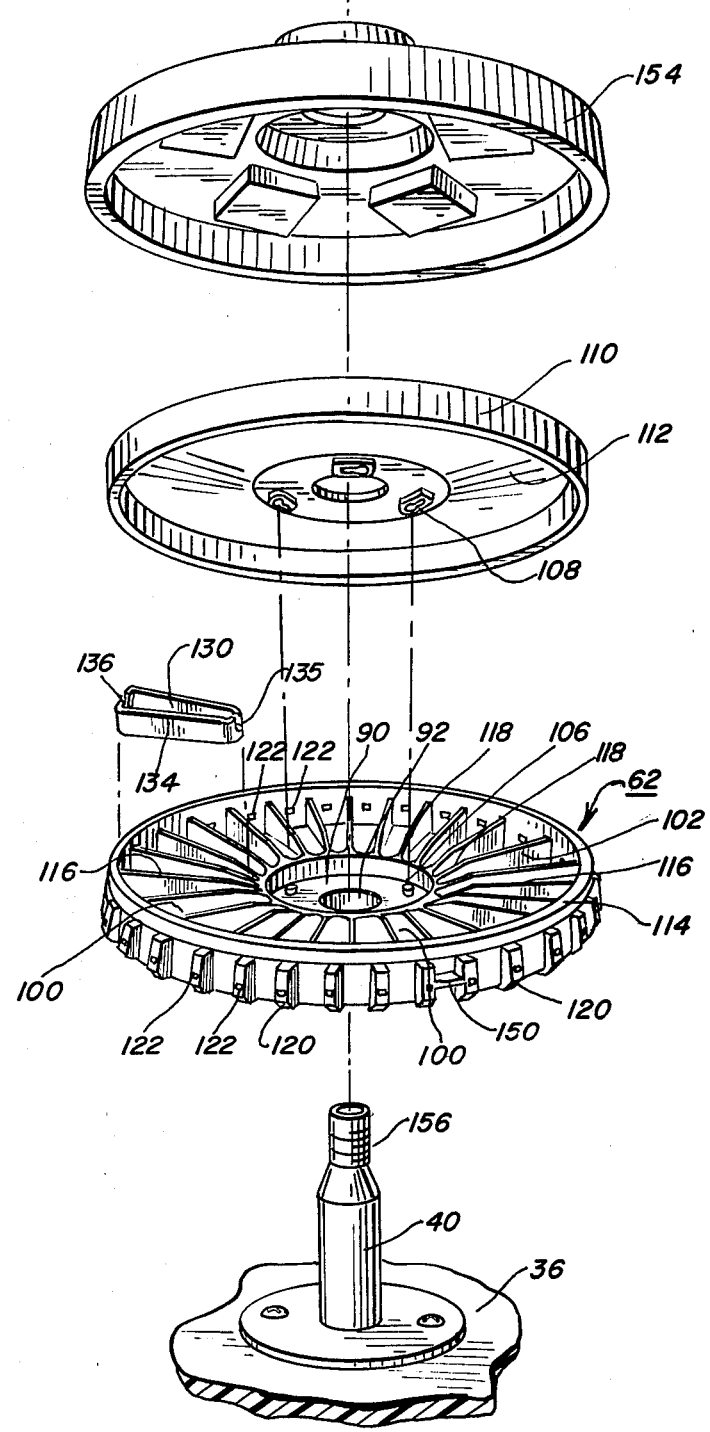
FIG. 3 is an exploded perspective view of a carrier member constructed in accordance with the principles of the present invention for use with the centrifugal fast analyzer of FIGS. 1 and 2.

Referring to FIGS. 3-5, a circular carrier member 62 is illustrated therein, for use with the centrifugal analyzer of FIGS. 1 and 2. Carrier member 62 is preferably a unit molded from plastic, such as polystyrene or acrylic, and being physically substitutable for the type of transfer disc illustrated in U.S. Pat. No. 3,856,470 and presently used with the ROTOCHEM ® IIa centrifugal fast analyzer. Carrier member 62 is generally circular (i.e., disc-shaped) having a central hub portion 90 which defines a central opening 92. A resilient O-ring 96 is interposed within a recess defined by hub 94, to form a liquid seal with shaft 40 when the shaft 40 is within opening 92.

Carrier member 62 has a main body portion 98 which defines a plurality of slots 100, each of which slots is bounded by an inner wall 101, a pair of side walls 102 and an outer wall 104. The slots are generally pie-shaped and although no limitation is intended, the carrier member may contain 36 slots, 35 of which are utilized for actual analysis while one slot is utilized for calibration purposes.

A number of pins 106, carried by hub 90, are equally spaced as illustrated on FIG. 4. Pins 106 are utilized for engagement with the keyhole slots 108 of a plastic cover member 110. The dimensions are such that the bottom surface 112 of cover member 110 abuts top surface 114 of the outer ring 115 which forms walls 104. While the top surface 116 of walls 102 is generally parallel to the bottom surface 117 (see FIG. 6), the inside portion closest to hub 90 has an angle 118 for enabling the operator to grasp an insert and for effective flushing of the system (discussed below).

Along the outer periphery of carrier member 62 there are radially extending indexing ribs 120, centrally positioned with respect to each slot and defining apertures through the peripheral wall of the carrier member, whereby the slots 100 each communicate through apertures 122 to the outside of the carrier member 62.

Each of slots 100 is adapted to receive an insert 130 (FIGS. 3 and 8-10). Inserts 130 are generally pie-shaped container-like inserts and have a bottom 131, an inside end wall 132, an outside end wall 133 and side walls 134. Side walls 134 taper outwardly from inside wall 132 to outside wall 133. Inside wall 132 and outside wall 133 define slots 135, 136, respectively, which extend down from the top of the insert approximately one-third of the height of the insert. Slot 136 is utilized for transfer of the constituents, during centrifugation, from the insert through the slot 136, through aperture 122 and into the respective slot 140 (FIGS. 4 and 6) defined by cuvette ring 60. The inside 141 of outside wall 133 is tapered slightly upwardly and outwardly, for example, 1°, so that during rotation the centrifugal forces will urge the constituents to flow from the insert along the inside of outside wall 133 and outside via slot 136.

Slot 135 defined by the inside end 132 of insert 130 is utilized in the flushing operation. Thus after the reaction is completed, a fluid, such as air and/or wash solution, is introduced through openings defined by shaft 40, and the fluid is forced into the inserts via slots 135 and into the slots 140 of cuvette ring 60 via slots 136 and apertures 122. The angle 118 provides a suitable opening for the passage of the flushing fluid to the slots 135.

Figure 6:
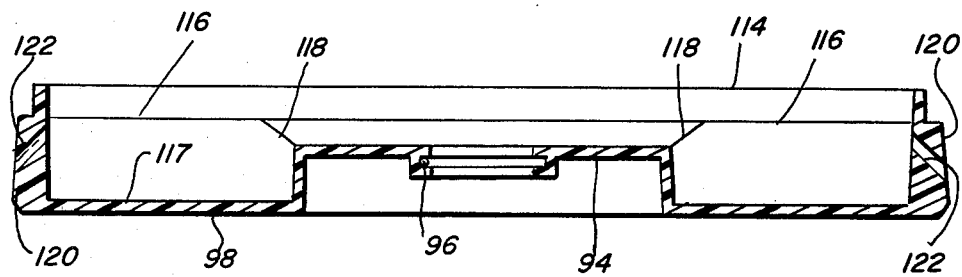
FIG. 6 is a cross-sectional view taken along the plane of the line 6—6 of FIG. 4.
Figure 8:
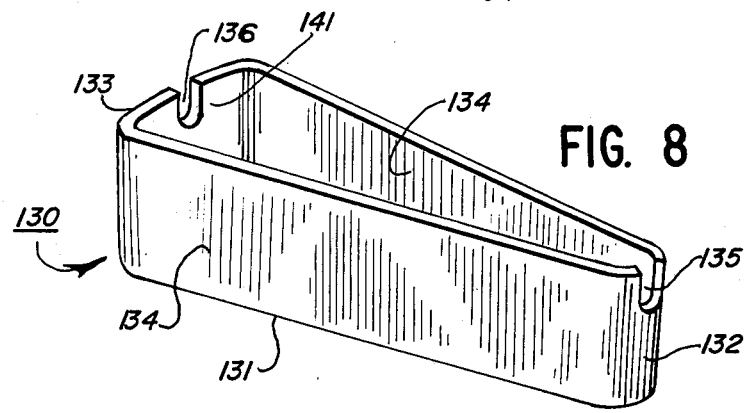
FIG. 8 is a perspective view of an insert adapted for positioning within the carrier member of FIG. 3.
Figure 9:
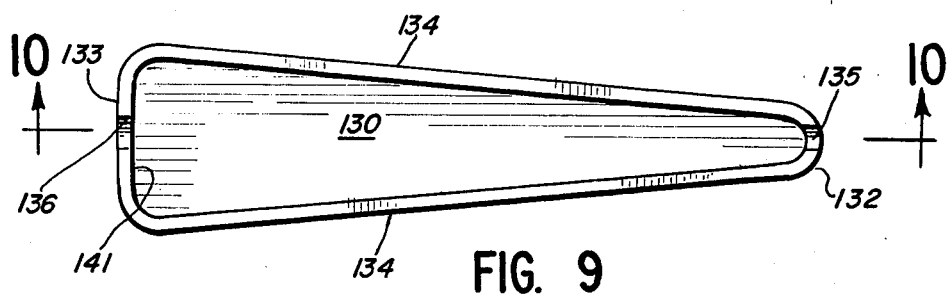
FIG. 9 is a top plan view thereof.
Figure 10:
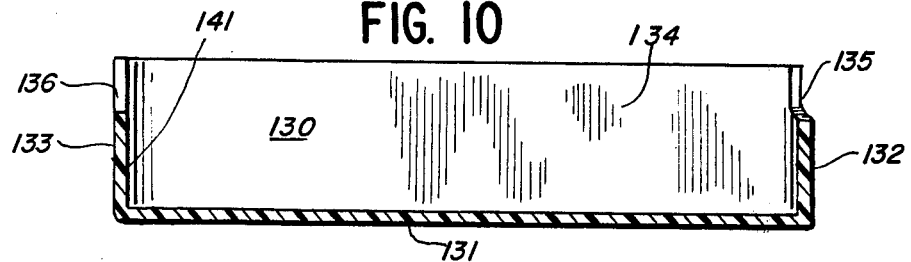
FIG. 10 is a cross-sectional view thereof, taken along the plane of the line 10—10 of FIG. 9.

The assembly of the carrier member 62 with the cuvette ring 60 is illustrated in FIG. 4. It can be seen that indexing ribs 120 extend into respective slots 140. Referring to FIG. 6, it can be seen that glass rings 70 and 72, when in place above and below cuvette ring 60, form, with slots 140, the cuvette cells, and enable the centrifuged components within the cuvette cells to be optically analyzed through the glass rings. Cuvette ring 60 is provided with a siphon slot 142 adjacent each slot 140 and communicating with the slot 140, for enabling exhaust of the analyzed components and wash solution when the analysis is completed. Further, cuvette ring 60 is preferably formed of material having good thermal conductivity and carrying an electrical conductor for heating purposes as disclosed in U.S. Pat. No. 3,856,470. Thus all of the structure and advantages of the cuvette ring disclosed in U.S. Pat. No. 3,856,470 may be utilized in connection with the present invention.

Some or all of the inserts 130 may be lined or coated on the inside or a portion of the inside thereof with an agent for use in an in vitro diagnostic test. Such an agent may be precoated on the inside surface of insert 130 or on a portion thereof. For example, insert 130 may carry a separating member to form a forward chamber that is precoated and a rear chamber that is not coated. The sample to be assayed would be introduced into the rear chamber.

Thus the carrier member including the precoated inserts could be used to perform various assays in the centrifugal fast analyzer, with the operator only having to introduce the sample to be assayed. For example, heterogeneous enzyme immunoassays could be performed. To this end, the insert 130 is precoated with antibodies directed against an analyte.

The portion of the insert 130 to be precoated must be formed of a material that is receptive to the coating. Although polypropylene is inert to some coating processes, the surface of the polypropylene may be activated by treatment with a solvent and thereupon accept a coating. Polystyrene and polycarbonate are plastics which are also receptive to such precoating.

In the operation of the system, in a specific example inserts 130 are loaded into slots 100 of carrier member 62. Inserts 130 have an inside precoating of an antibody. An aliquot of serum to be assayed is introduced into the insert and an enzyme coupled to an antigen directed against the antibody coating is also added to the insert. Plastic cover 110 is then placed on top of carrier member 62 and twisted shut, with pins 106 entering into and being locked within keyhole slots 108. The covered carrier member is placed into an incubator, and incubated at an elevated temperature (for example, 37° C.) for a predetermined time period, for example, in the range of from 30 minutes to 4 hours. Thereafter, the carrier member is placed into a centrifuge and spun so that anything in liquid form will be centrifuged out of the inserts into a waste receptacle.

Thereafter, cover 110 is removed and a buffer solution, such as 1 ml phosphate, is added to each insert to extract excess sample and enzyme that has not bound. The wash solution is centrifuged out and one-half ml enzyme substrate solution is added to each insert by means of a pipette or by automated means. Carrier member 62 is covered with cover 110 and then returned to the incubator and incubated for another 10 or 15 minutes at a preselected elevated temperature. Cover 110 is removed and a stopping solution, such as 0.2 ml of hydrochloric acid, is added to each insert. Water is added to the zero position insert for calibration purposes. The carrier member 62 is covered again with cover 110 and is placed into centrifugal fast analyzer 10 by lifting top cover 28 and placing the carrier member 62 onto rotor 36 in the same manner that the transfer disc in the ROTOCHEM ® IIa centrifugal fast analyzer is placed onto the rotor. An indexing pin 150 carried by carrier member 62 is aligned with the receiving slot of cuvette ring 60 in order to align carrier member 62 appropriately. Pressure cap 154 is then screwed onto threaded portion 156 of rotor shaft 140 and top cover 28 is lowered and pressed downward until it locks in place. The appropriate program is set and the system is run in the same manner that the ROTOCHEM ® IIa centrifugal fast analyzer is usually run.

After the wash cycle is completed, the top cover 28 is raised, pressure cap 154 is unscrewed, and the carrier member 62 is removed from the rotor. The carrier member 62 is brought to a wastebasket, plastic cover 110 is removed, the carrier member 62 is inverted toward the wastebasket and by hitting carrier member 62 sharply inserts 140 should fall out into the wastebasket. Carrier member 62 can then be reused with new inserts.

Although an illustrative embodiment of the invention has been shown and described, it is to be understood that various modifications and substitutions may be made by those skilled in the art without departing from the novel spirit and scope of the present invention.

That which is claimed is:

1. A centrifugal analyzer which comprises:
   a rotor including a rotatable shaft;
   a circular cuvette ring having an inner wall defining a central opening and slots extending radially outwardly from the central opening, said cuvette ring being adapted for positioning on said rotor encircling said shaft;
   a circular carrier member defining a central aperture and being adapted for positioning within the central opening of the cuvette ring, with the shaft extending through the central aperture of the carrier member;
   said carrier member defining on its top surface a plurality of slots for receiving constituents to be centrifuged;
   said carrier member having a peripheral wall for facing the inner wall of the cuvette ring, said peripheral wall defining apertures which communicate with the slots defined by the cuvette ring when the carrier member is positioned within the central opening of the cuvette ring, each of said apertures being in communication with one of said carrier member slots;
   a plurality of disposable container-like inserts, each of which is adapted for positioning within one of said carrier member slots, each of said inserts being adapted to receive directly constituents to be centrifuged and having means for enabling centrifugal transfer of the constituents in the insert to an aperture defined by the peripheral wall of said carrier member, for transfer of the constituents into a respective slot defined by the cuvette ring.

2. A device as described in claim 1, said inserts having an inside end wall, an outside end wall, a bottom and a pair of side walls, with the side walls extending outwardly from the inside end wall to the outside end wall, each insert being adapted for positioning within a generally pie-shaped carrier member slot with said inside end wall facing toward said central aperture and the outside end wall facing toward said peripheral wall.

3. A device as described in claim 2, said centrifugal transfer enabling means comprising said outside end wall having an angled inside surface with an opening defined by said outside end wall, said outside end wall opening being adapted for communication with a slot defined by the cuvette ring when the insert is positioned in a carrier member slot.

4. A device as described in claim 1, said carrier member slots comprising generally pie-shaped slots defined by said walls which taper radially outwardly.

5. A device as described in claim 1, including a resilient ring concentrically disposed within the central aperture of the carrier member and serving to form a liquid seal between the shaft and the carrier member.

6. A device as described in claim 1, said carrier member comprising an integrally-molded plastic member.

7. A device as described in claim 6, said carrier member slots comprising generally pie-shaped slots defined by side walls which taper radially outwardly.

8. A device as described in claim 7, said inserts having an inside end wall, an outside end wall, a bottom and a pair of side walls, with the side walls extending outwardly from the inside end wall to the outside end wall, each insert being adapted for positioning within a generally pie-shaped carrier member slot with said inside end wall facing toward said central aperture and the outside end wall facing toward said peripheral wall.

9. For use with a centrifugal analyzer comprising a rotor including a rotatable shaft, a circular cuvette ring having an inner wall defining a central opening and slots extending radially outwardly from the central opening with the cuvette ring being positioned on the rotor encircling the shaft, the invention comprising, in combination:
   a circular carrier member defining a central aperture and being adapted for positioning with the central opening of the cuvette ring, with the shaft extending through the central aperture of the carrier member;
   said carrier member defining on its top surface means for receiving a plurality of disposable container-like inserts;
   said carrier member having a peripheral wall for facing the inner wall of the cuvette ring, said peripheral wall defining apertures which communicate with the slots defined by the cuvette ring when the carrier member is positioned within the central opening of the cuvette ring, each of said apertures being in communication with said receiving means.

10. A device as described in claim 9, said receiving means comprising a plurality of radially extending slots.

11. A device as described in claim 9, including a plurality of disposable container-like inserts, each of which is adapted for positioning within one of said carrier member slots, each of said inserts being adapted to receive directly constituents to be centrifuged and having means for enabling centrifugal transfer of the constituents in the insert to an aperture defined by the peripheral wall of said carrier member, for transfer of the constituents into a respective slot defined by the cuvette ring.

12. A device as described in claim 11, in which at least a portion of the insert carries a precoating of one of said constituents for use in an in vitro diagnostic test.

13. A device as described in claim 11, said inserts having an inside end wall, an outside end wall, a bottom and a pair of side walls, with the side walls extending outwardly from the inside end wall to the outside end wall, each insert being adapted for positioning within a generally pie-shaped carrier member slot with said inside end wall facing toward said central aperture and the outside end wall facing toward said peripheral wall.

14. A device as described in claim 13, said centrifugal transfer enabling means comprising said outside end wall having an angled inside surface with an opening defined by said outside end wall, said outside end wall opening being adapted for communication with a slot defined by the cuvette ring when the insert is positioned in a carrier member slot.

15. A device as described in claim 9, said receiving means comprising generally pie-shaped slots defined by side walls which taper radially outwardly.

16. A device as described in claim 9, including a resilient ring concentrically disposed within the central aperture of the carrier member and serving to form a liquid seal between the shaft and the carrier member.

17. A device as described in claim 9, said carrier member comprising an integrally-molded plastic member.

18. For use with a centrifugal analyzer comprising a rotor including a rotatable shaft, a circular cuvette ring having an inner wall defining a central opening and slots extending radially outwardly from the central opening with the ring being positioned on the rotor encircling the shaft, a circular carrier member defining a central aperture and being adapted for positioning within the central opening of the cuvette ring, with the shaft extending through the central aperture of the carrier member, said carrier member defining on its top surface a plurality of slots for receiving constituents to be centrifuged, said carrier member having a peripheral wall for facing the inner wall of the cuvette ring, said peripheral wall defining apertures which communicate with the slots defined by the cuvette ring when the carrier member is positioned within the central opening of the cuvette ring, each of said apertures being in communication with one of said carrier member slots, the invention comprising, in combination:

a plurality of disposable container-like inserts, each of which is adapted for positioning within one of said carrier member slots, each of said inserts being adapted to receive directly constituents to be centrifuged and having means for enabling centrifugal transfer of the constituents in the insert to an aperture defined by the peripheral wall of the carrier member, for transfer of the constituents into a respective slot defined by the cuvette ring.

19. A device as described in claim 18, said inserts having an inside end wall, an outside end wall, a bottom and a pair of side walls, with the side walls extending outwardly from the inside end wall to the outside end wall, each insert being adapted for positioning within a generally pie-shaped carrier member slot.

20. A device as described in claim 19, said centrifugal transfer enabling means comprising said outside end wall having an angled inside surface with an opening defined by said outside end wall, said outside end wall opening being adapted for communication with a slot defined by the cuvette ring when the insert is positioned in a carrier member slot.

21. A device as described in claim 18, at least a portion of said inserts carrying a precoating of one of said constituents for use in an in vitro diagnostic test.

22. A disposable insert for use with a carrier member of a centrifugal analyzer, which comprises:
a container having an inside end wall, an outside end wall, a bottom and a pair of side walls, said side walls extending outwardly from the inside end wall to the outside end wall, said insert being formed of a plastic material and being adapted to receive directly constituents to be centrifuged and to enable centrifugal transfer of the constituents in the insert to a separate cuvette member.

23. A disposable insert as described in claim 22, in which said outside end wall has an inside surface that is sloped upwardly and outwardly with respect to the inside surface of said bottom.

24. A disposable insert as described in claim 23, in which said outside end wall defines a slot.

25. An insert as described in claim 24, in which said inside end wall defines a slot.

26. An insert as described in claim 22, in which at least a portion of the interior of said insert carries a precoating of an agent for use in an in vitro diagnostic test.

27. An insert as described in claim 22, including means for separating a front portion of said insert adjacent said outside end wall from a rear portion of said insert adjacent said inside end wall.

28. An insert as described in claim 26, in which only said front portion is precoated with an agent for use in an in vitro diagnostic test.

29. A disposable insert for use with a carrier member of a centrifugal analyzer, which comprises:
a container having an inside end wall, an outside end wall, a bottom and a pair of side walls, said side walls extending outwardly from the inside end wall to the outside end wall;
said insert being formed of a plastic material and being adapted to receive directly constituents to be centrifuged and to enable centrifugal transfer of the constituents in the insert to a separate cuvette member;
said outside end wall defining a slot and said inside end wall defining a slot;
means for separating a front portion of said insert adjacent said outside end wall from a rear portion of said insert adjacent said inside end wall; and
only said front portion being precoated with an agent for use in an in vitro diagnostic test.

30. An insert as described in claim 29, in which said outside end wall has an inside surface that is sloped upwardly and outwardly with respect to the inside surface of said bottom.

31. A method for chemical analysis which comprises the steps of:
providing a plurality of disposable container-like inserts in which a portion of the inside thereof is coated with an agent for use in an in vitro diagnostic test;
placing said inserts into a carrier member which is adapted for rotation in a centrifugal fast analyzer;
adding to said inserts samples to be tested;
placing said carrier member in a centrifugal analyzer; and
rotating said carrier member to transfer centrifugally the constituents in the inserts to a cuvette member.

32. A method for chemical analysis as described in claim 31, including the step of, after rotating said carrier member, removing and disposing of said container-like inserts from said carrier member.

33. A method as described in claim 31, in which said precoated agent comprises antibodies directed against an analyte.

34. A method for chemical analysis using a centrifugal analyzer comprising a rotor including a rotatable shaft, a circular cuvette ring having an inner wall defining a central opening and slots extending radially outwardly from the central opening with the ring being positioned on the rotor encircling the shaft, the method comprising the steps of:
providing a circular carrier member which defines a central aperture and also defines on its top surface a plurality of slots;
providing a plurality of disposable container-like inserts;
placing said inserts into said carrier member slots;
adding to said inserts samples to be tested;
positioning said carrier member within the central opening of the cuvette ring, with said shaft extending through the central aperture of the carrier member; and
rotating said circular cuvette ring and said carrier member together.

* * * * *